(12) United States Patent
Jorgenson et al.

(10) Patent No.: US 6,208,897 B1
(45) Date of Patent: Mar. 27, 2001

(54) METHOD AND APPARATUS FOR MONITORING AND TREATING SUDDEN INFANT DEATH SYNDROME

(75) Inventors: Dawn Billie Jorgenson, Seattle; Bradford E Gliner, Issaquah, both of WA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/300,263

(22) Filed: Apr. 27, 1999

(51) Int. Cl.$^7$ ........................................................ A61N 1/39
(52) U.S. Cl. ................................................ 607/5; 128/898
(58) Field of Search .................... 607/4, 5, 6; 600/511, 600/529, 544, 483–486, 480; 128/898

(56) References Cited

U.S. PATENT DOCUMENTS

| | | |
|---|---|---|
| 4,306,567 | 12/1981 | Krasner . |
| 4,738,266 | 4/1988 | Thatcher . |
| 4,851,816 | 7/1989 | Macias et al. . |
| 5,277,194 | 1/1994 | Hosterman et al. . |
| 5,317,767 | 6/1994 | Hargest et al. . |
| 5,360,008 | 11/1994 | Campbell, Jr. . |
| 5,483,711 | 1/1996 | Hargest et al. . |
| 5,505,199 | 4/1996 | Kim . |
| 5,515,865 | 5/1996 | Scanlon . |
| 5,615,688 | 4/1997 | O'Dwyer . |
| 5,684,460 | 11/1997 | Scanlon . |
| 5,774,055 | 6/1998 | Pomerantz . |
| 5,787,534 | 8/1998 | Hargest et al. . |
| 5,825,293 | 10/1998 | Ahmed et al. . |
| 6,064,910 | * 5/2000 | Andersson et al. .................... 607/20 |

OTHER PUBLICATIONS

Prolongation of the QT Interval and the Sudden Infant Death Syndrome; 338 (24): 1709–1714 (1998).

* cited by examiner

*Primary Examiner*—Jeffrey R. Jastrzab
(74) *Attorney, Agent, or Firm*—Cecily Anne Snyder

(57) ABSTRACT

This invention relates generally to a device for monitoring an infant for the onset of sudden infant death syndrome (SIDS), detecting the onset of SIDS and providing immediate treatment. In the broadest sense, the invention includes an apparatus for detecting and treating SIDS. The apparatus comprises a data gatherer for monitoring an infant parameter, a controller for communicating with the data gatherer, an energy source operable to power the data gatherer for monitoring the infant parameter and further operable to provide energy to an energy delivery system which is operable to deliver an electric shock from an energy source to an electrode interface, and an alarm which is activated by the controller for alerting a remote caregiver to the onset of symptoms associated with SIDS. The invention also relates to a method of operating a SIDS monitor. The method comprises the steps of monitoring an infant parameter, determining whether the monitored parameter is an acceptable value. If the monitored parameter is an acceptable value, then an alarm is activated to alert a caretaker of the onset of SIDS symptoms, if the monitored parameter is within an acceptable value, then continuing to monitor the infant parameter.

24 Claims, 2 Drawing Sheets

METHOD AND APPARATUS FOR MONITORING AND TREATING SUDDEN INFANT DEATH SYNDROME

BACKGROUND OF THE INVENTION

1. Field of the Invention

This invention relates generally to a device for monitoring an infant for the onset of sudden infant death syndrome (SIDS), detecting the onset of SIDS and providing immediate treatment. Treatment could include instructions for administering cardiopulmonary resuscitation (CPR) as well as delivery of a defibrillation pulse from an automatic or semi-automatic external defibrillator (AED). The device may be a SIDS monitor as well as a SIDS trainer, or a SIDS monitor which has the ability to function as a trainer.

2. Description of the Prior Art

SIDS is a phenomenon which has been used to describe the sudden unexpected and unexplained death of an infant. Infant mortality is classified as SIDS when, despite a thorough investigation, no explanation can be found for the death of the infant. Currently, the incident of SIDS in the United States is approximately 1.6 per 1000 live births; upwards of 10,000 deaths per year in the United States alone. SIDS is the most common cause of death among children from one to six months of age.

Because SIDS is identified in situations where no explanation for the death can be found, the potential causes of SIDS has been largely speculative. Potential causes include cardiac disorders, respiratory abnormalities, gastrointestinal diseases, metabolic disorders, injury and child abuse.

Many devices have been developed that provide a way to monitor an infant for the onset of SIDS by detecting cessation of movement, cessation of respiration or detection of urination that may accompany agonal movement. Other devices have been developed to prevent SIDS from occuring, such as by providing an oxygenated mattress. The following summarizes a selection of previously patented approaches to SIDS detection and/or prevention.

U.S. Pat. No. 4,306,567 to Krasner describes a detector and monitoring device to be used to detect the onset of SIDS. The device of Krasner is an apnea monitor that is non-contacting. The device of Krasner detects the acoustical signal generated as a function of the breathing cycle to determine whether or not the infant is breathing.

U.S. Pat. No. 4,738,266 to Thatcher describes an apnea monitor. The device of Thatcher is in the form of a crib with a hood over the top. The hood collects the exhaled breath of in infant. Infrared energy is emitted into the hood and monitored such that, as long as $CO_2$ is present in the hood (from exhaled breath), the device continues in monitoring mode. However, if the level of $CO_2$ decreases there will be a corresponding change in the IR activity and an alarm will sound.

U.S. Pat. No. 4,851,816 by Macias et al. is directed to an apparatus for detecting the moment of urination for an infant. According to Macias, it is estimated that 85% of SIDS victims have some sort of agonal motor activity. Since urination would be expected to accompany agonal motor activity, by detecting the moment of urination, a parent would be alerted to the onset of SIDS and would attend to the infant. Additionally, a cardioverter is provided to stimulate conduction of tetanic contraction in an offending muscle by stimulating reflexive hyperdistension. One drawback of the device described by Macias is that it cannot detect the difference between urination as a result of agonal movement and urination generally. As a result, a parent might be watchful initially, but after a few days or weeks, would likely either discontinue using the device or would not respond immediately thereby eliminating the potential likelihood of discovering SIDS within the first few minutes.

U.S. Pat. No. 5,277,194 by Hosterman et al. is directed to a breathing monitor and stimulator. Hosterman provides an apparatus that is worn around the chest of the infant and monitors the breathing pattern. A bladder is provided in the device that can be cyclically operated to induce breathing when either a change in breathing rate is detected or cessation of breathing. An alarm may also sound when the device detects a change in breathing pattern, thus alerting a primary caregiver that a problem exists.

U.S. Pat. Nos. 5,317,767; 5,483,711 and 5,787,534 are a series of patents to Hargest et al. directed to a safety pad for use in a crib which prevents SIDS by ensuring an oxygenated breathing space beneath the infant. As noted in Hargest et al., the weight of an infant's head relative to the rest of the body is quite high. Further, the next muscles of an infant are not well developed. Thus, if an infant is placed in the prone position for a nap (i.e., on their stomach) and they attempt to turn their head from one side to the other they could become stuck with their face pressed into the mattress due to lack of strength of their neck muscles. This would result in suffocation. Thus, the apparatus of Hargest et al. would prevent such suffocation by providing an oxygen saturated mattress.

U.S. Pat. No. 5,505,199 to Kim is a monitor which determines oxygen saturation and movement. When a change in oxygen saturation is detected along with lack of movement, the device brings a video image of the infant into the parent's room, thus enabling the parents to see the condition of the child.

U.S. Pat. No. 5,615,688 to O'Dwyer is directed to an apnea detection device. A strap is provided for the wearer's chest. The strap provides a detection mechanism in a housing for monitoring the respiration of an infant. A transmitter is also provided which transmits a signal to a receiver in the event that an anomoly in breathing is detected. Upon receipt of the signal from the transmitter the receiver emits an alarm to warn of the breathing anomoly.

U.S. Pat. No. 5,360,008 to Campbell Jr. is directed to a respiratory and cardiac monitor. Campbell Jr. monitors the electromagnetic permeability of the trunk, which changes during the respiratory cycle, to detect the respiratory cycle and cardiac cycle. A receiver/transducer is worn on a belt by the patient. The receiver/transducer communicates with a transmitter/transducer which is mounted on a suitable housing and disposed within close proximity to the receiver/transducer. An electronic signal which is modulated in its amplitude by the varying permeability of the patient's body (occurring during the respiration process) is sent by the receiver/transducer to the transmitter/transducer. The received signal is amplified and filtered to obtain a signal corresponding to the patient's pulse and the patient's respiration.

U.S. Pat. Nos. 5,515,865 and 5,648,460 to Scanlon is directed to a fluid-filled sensing pad for supporting an infant. The pad uses a transducer to detect movement or acoustic activity. When no movement or acoustic activity is detected a stimulator is activated to move the infant.

U.S. Pat. No. 5,774,055 by Pomerantz is directed to an infant monitoring device comprising a sensor connected to an alarm. The sensor can alert a parent if the infant assumes a predetermined position. Alternatively, the sensor can alert a parent if the infant is in the same position for a period of time exceeding an amount provided for by the sensor.

U.S. Pat. No. 5,825,293 to Ahmed et al. is directed to a method and apparatus for monitoring breathing magnetically. A magnet is placed so that it moves in common with either the abdominal wall or the chest wall. A receiver is placed, for example, at the edge of the crib. As the magnet moves up and down with the infant's respiration, the receiver detects the resulting change in distance from the receiver. If the infant stops breathing, no change in distance is detected and an alarm is sounded.

One disadvantage of the prior art solutions is that the systems are easily activated by conditions other than the onset of SIDS. These false alarms could condition the caretaker to be less diligent in responding to the alarm and might result in an actual SIDS episode escaping detection.

As is evident by the prior art solutions, it has been hypothecated that SIDS is the result of apnea or suffocation. Recently, however, a study by Schwartz et al. indicated that, in many cases, SIDS victims have a history of long QT syndrome. Schwartz et al. "Prolongation of the QT Interval and the Sudden Infant Death Syndrome" *NEJM* 338(24) :1709–1714 (1998). Schartz et al. recorded ECGs for 34,442 newborn babies over a period of 18 years. The discovered that the infants that died from SIDS typically had a longer corrected QT interval that the survivors. Long QT is known to be a marker of cardiac electrical instability which indicates a predisposition to fatal cardiac arrhythmias. As a result, even if SIDS were detected by using one of the prior art solutions, a caretaker would stand by helpless to provide assistance and would have to wait until emergency medical personnel arrived.

As will be appreciated by those skilled in the art, for those SIDS occurrences that result from a cardiac arrhythmia, blood may no longer be pumping effectively. If blood is no longer pumping effectively, it is imperative that effective resuscitative efforts begin as soon after the onset of the condition as possible since brain damage can occur after the brain is deprived of oxygen for four to six minutes. Resuscitative efforts include CPR and defibrillation if a shockable cardiac arrhythmia exists.

What is needed is a device that monitors the respiration and/or cardiac activity of an infant identified with long QT syndrome who may be at high risk for SIDS and then provides an effective mechanism for initiating treatment until an emergency medical technician (EMT) arrives.

SUMMARY OF THE INVENTION

This invention is directed to a SIDS monitor. The monitor has an energy source, an interface and an audible sound generator, wherein the interface is in electrical communication with the energy source and a detector for detecting the onset of SIDS. The detector may be a cardiac monitoring device, an electroencephalogram (EEG) monitoring device, a respiratory monitoring device, a pulse monitoring device, a pulse oximeter, or a combination thereof. The SIDS monitor includes the ability to function as an automatic or semi-automatic defibrillator (AED). The SIDS monitor also has an instruction generator which communicates with the audible sound generator. The SIDS monitor may also have a visual image generator which communicates with instruction generator. The instruction generator generates audible prompts, visual images, or a combination thereof.

In the broadest sense, the invention includes an apparatus for detecting and treating SIDS. The apparatus comprises a data gatherer for monitoring an infant parameter, a controller for communicating with the data gatherer, an energy source operable to power the data gatherer for monitoring the infant parameter and further operable to provide energy to an energy delivery system which is operable to deliver an electric shock from an energy source to an electrode interface, and an alarm which is activated by the controller for alerting a remote caregiver to the onset of symptoms associated with SIDS. The invention also relates to a method of operating a SIDS monitor. The method comprises the steps of monitoring an infant parameter, determining whether the monitored parameter is an acceptable value. If the monitored parameter is an acceptable value, then an alarm is activated to alert a caretaker of the onset of SIDS symptoms, if the monitored parameter is within an acceptable value, then continuing to monitor the infant parameter.

DESCRIPTION OF THE PREFERRED EMBODIMENTS

Figure 1:
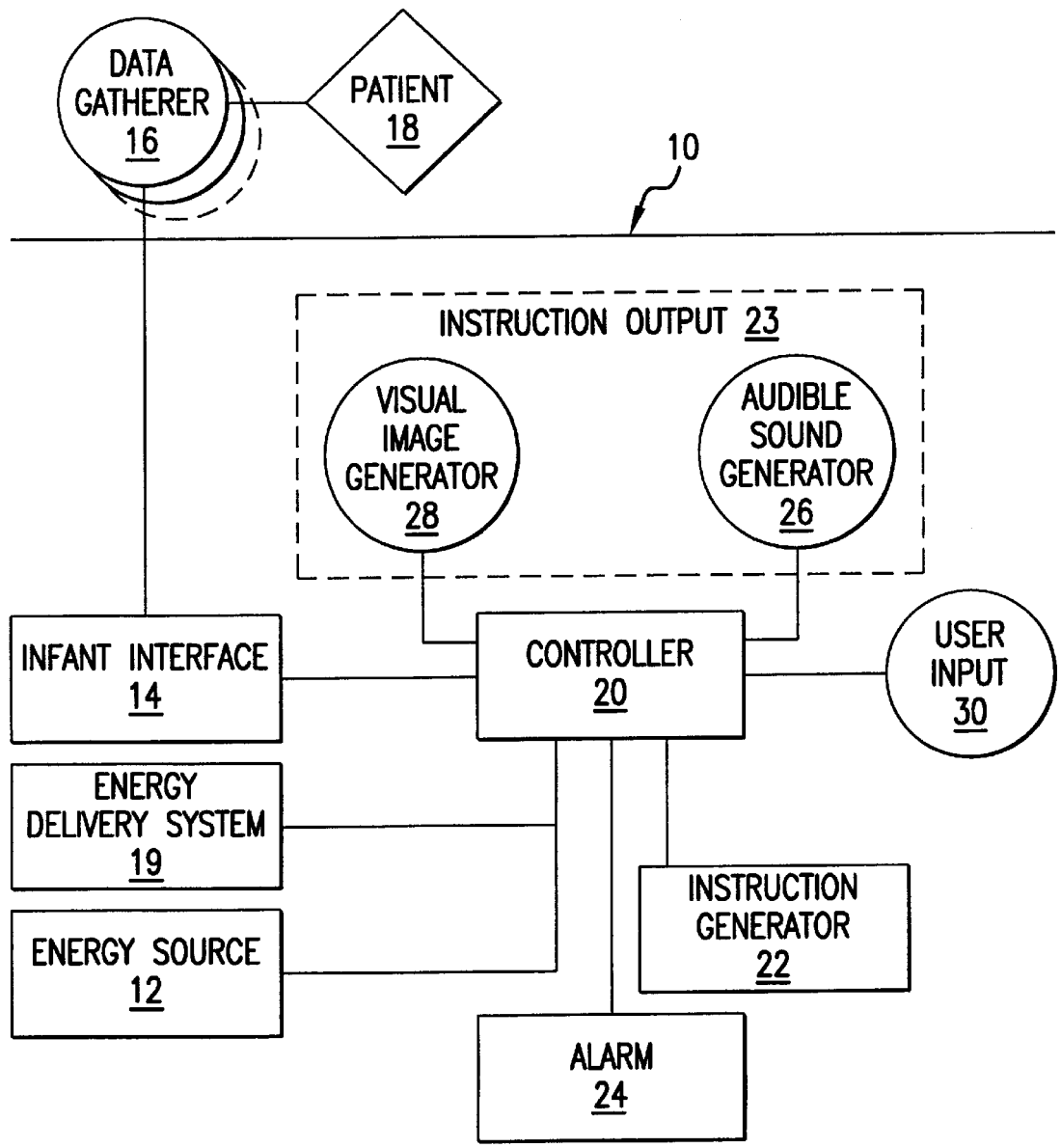
FIG. 1 is a diagrammatic representation of a SIDS monitoring system.

FIG. 1 is a schematic block diagram of a SIDS monitoring system 10 according to a preferred embodiment of this invention. The SIDS system 10 comprises an energy source 12. The energy source 12 powers the system during the monitoring phase and provides voltage or current pulses in the event the defibrillation function is deployed. An infant interface 14 is provided which connects the monitoring system 10 to the infant 18 by a monitoring connector of a data gatherer 16. The interface 14 is configured so that it receives input from one or more data gathering device connectors and defibrillator connectors. The monitoring connector may be a single connector or a plurality of connectors.

When the interface 14 is adapted to connect to defibrillation electrodes, the interface communicates with a controller 20 which operates to selectively connect and disconnect energy source 12 to and from a pair of defibrillation electrodes electrically attached to the infant 18 to provide electrotherapy to the infant.

The data gathering devices 16 are used to monitor biological parameters of the infant 18; the information gathered by the devices is transmitted to the monitor 10 for use in determining the onset of SIDS. For example, data gathering device 16 may be a pulse oximeter which is used to detect a change in blood oxygen level. Alternatively, a pulse detector may be provided to detect a cessation of the pulse. Cardiac monitoring electrodes may also be used to detect cardiac rhythm or EEG monitoring electrodes may be used to detect EEG.

It will be appreciated by those of skill in the art that a single set of electrodes can be used to monitor the cardiac function and then to deliver a defibrillation energy pulse, if required. In a preferred embodiment, however, a set of wireless monitoring electrodes are provided for monitoring. Ideally, the monitoring electrodes should be low cost and reusable.

Where separate cardiac monitoring electrodes are used, a separate set of defibrillation electrodes is provided in the event defibrillation is required. The defibrillation electrodes would not be deployed unless a shockable rhythm is detected by the monitor 10. The SIDS monitors 10 may have any one of the data gatherers, a combination of data gatherers, or all of the data gatherers 16 providing data to the controller 20 for determination of the onset of SIDS.

It is preferably, although not required, for data gathered using any of the above gatherers to be communicated to the SIDS monitor 10 without the use of wires. For example, appropriate mechanisms for communicating the data from the data gatherers includes, but is not limited to, light wave transmission (for example, IR, or other suitable light waves), radio wave transmission, audio wave transmission, or magnetic wave transmission. In the event the data gatherers 16 communicate data to the monitor 10 using these wireless techniques, it will be appreciated by those skilled in the art that interface 14 will be appropriately adapted to receive the information from the data gatherers 16.

Additionally, controller 20 performs a protocol using information from an instruction generator 22 to provide instructions to the SIDS monitor operator. The instruction generator 22 may also activate protocol changes being performed by the SIDS monitor 10 based on information received from the controller 22. For example, controller 22 may assess the rate of respiration or the nature of the cardiac rhythm detected, the amount of time that has passed or the number of consecutive, or total, shocks that have been delivered, or other information that may be provided in determining which protocol to follow. Additionally, the controller 22 may be operating based on a combination of stored or generated data and interactive data, which would be the case if the SIDS monitor was either a trainer or was being used in a training mode. The amount or level of instruction generated by the instruction generator 22 can be modified according to the particular needs of the end user or any protocol that may be followed by the organization controlling the operation of the SIDS monitor (for example, where the monitor 10 is available on a check-out basis from a local hospital).

Instructions may be delivered via a visual image generator 24, such as by displaying, among other things, commands to the user (either written or graphic representations). The visual image generator 28 may be, for example, a liquid crystal display (LCD). Additionally, an audible sound generator 26 may be provided that broadcasts audible commands from the instruction generator 22. Audible commands may include verbal commands directing the user in the proper sequence and timing for administering CPR or instructions for enabling the defibrillator functionality. Activation of the visual image generator 28 and the audible sound generator 26 is controlled by the controller 20 in response to the information received from the instruction generator 22. Instruction generator 22 may be a set of software commands performed by controller 20.

An alarm 24 is provided that communicates with the user when the SIDS monitor 10 detects the onset of SIDS related symptoms. The alarm 24 receives instructions from the controller. The alarm 24 may either be associated with the audible sound generator 26 such that an audible alarm is generated in the vicinity of the infant 18 and the monitor 10 when the monitor detects the onset of SIDS. In a more preferred embodiment, the alarm 24 functions like a silent alarm by activating a system to alert a remote caretaker that the infant 18 is in distress. In an even more preferred embodiment, the alarm 24 activates a pager, or similar device, which is carried by the caretaker so that the caretaker will be alerted to the infant distress even when the caretaker is outside audible range of the SIDS monitor 10.

Where the monitor 10 is set-up provide defibrillator functionality on an automatic basis, it will be appreciated that the device will begin AED functionality without user intervention as described above. However, the device will, ideally, still provide some mechanism to advise the caretaker that the defibrillation operation has begun.

A memory device (not shown) may be provided for maintaining an active record of the monitored infant parameters for a period of time leading up to the onset of the SIDS symptoms, as well as a record of any parameters exhibited until the infant is transferred to an advance life care system. In a preferred embodiment, the memory device is either removable or can be downloaded from the monitor 10, for example with the use of an IRDA port. Further, the memory should be capable of storing at least 3 hours of information, more preferably 60 minutes of data. In order to conserve storage space, it is anticipated that the memory will be written over as new data becomes available such that the data available on the device at any given time represents only the most recent data.

Figure 2:
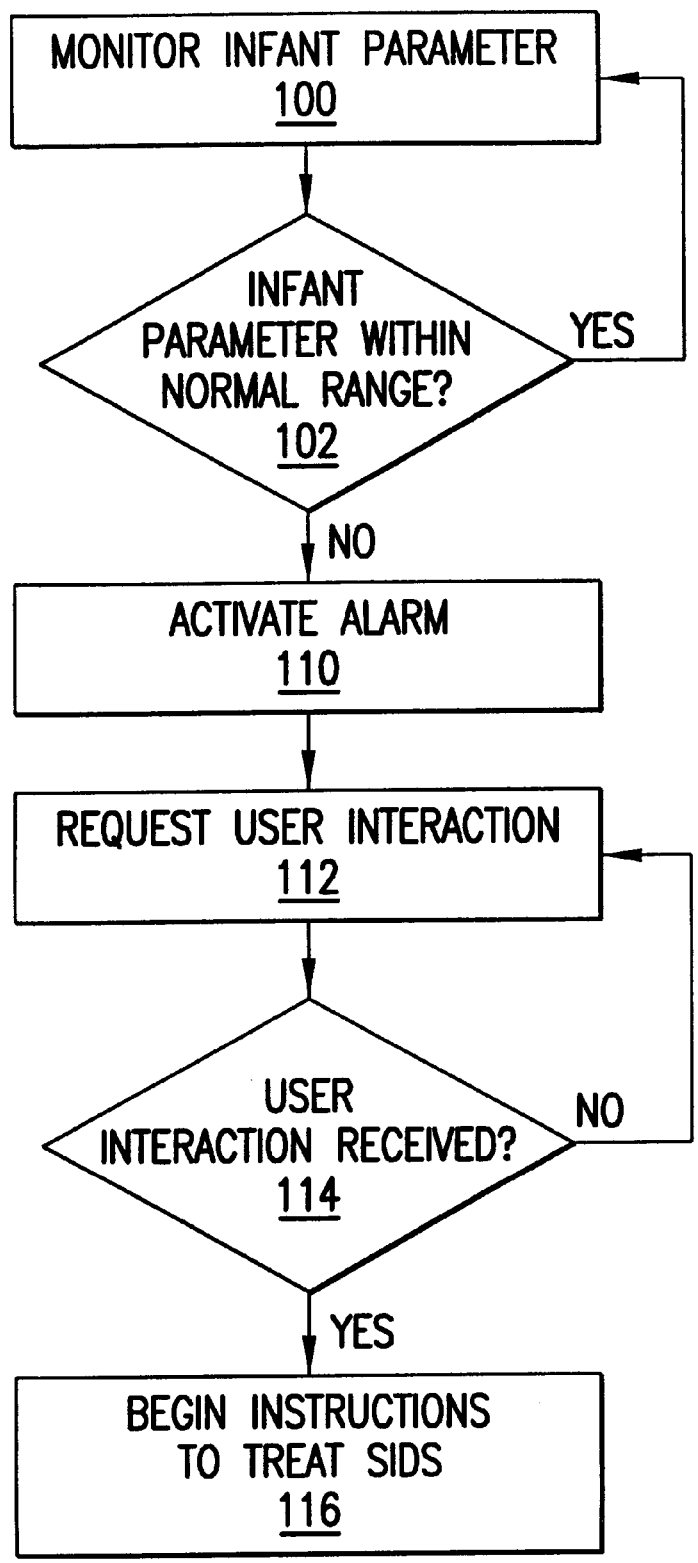
FIG. 2 is a flow chart demonstrating a SIDS monitor operating to gather information from the infant, detect the onset of SIDS and begin delivery of instructions to a caregiver for treating the infant.

Turning to FIG. 2, a flow chart demonstrates the operation of a SIDS monitor 10. At least one infant parameter is monitored 100. As discussed above, monitored parameters include monitored biological activities. These biological activities include, but are not limited to, respiration, heart rate, cardiac signal, EEG, and blood oxygen level. As described above, the infant parameter may be blood oxygen level, rate of respiration, cardiac signal, EEG signal, or pulse.

The monitor 10 receives the monitored patient parameter information and determines whether the parameter is within a normal range 102. If the parameter is within a normal range, the monitor continues to monitor infant parameter 100 using real time data. The real time data can be sampled either continuously or at a reasonable sample rate. If at any time during the monitoring process the infant parameter is not within the normal range 102, the monitor 10 activates an alarm 110. As described above, the alarm could either be an audible alarm issued from the monitor 10 or the activation of a remote device such as a pager. The monitor 10 will then begin requesting the user to indicate his or her presence 112. Presence may be indicated by, for example, providing user input at 30. If user interaction is not received, then the monitor 10 will continue to request interaction. In a preferred embodiment, if user interaction is not detected within, for example, 2 minutes, an audible alarm will be generated. Additionally or in the alternative, the monitor 10 may activate a 911 system in order to ensure that medical treatment is received. As will be appreciated by those of skill in the art, the amount of time for response as well as the point at which a 911 system is activated could be modified depending upon the needs of the particular end user. For a detailed explanation of a Communication Network System used for defibrillators, see U.S. Pat. No. 5,782,878 to Morgan et al., the specification of which is incorporated herein.

As will be appreciated by those of skill in the art, the monitor 10 may be configured such that the 911 system is activated upon detection of infant distress (at step 110). However, such a set-up may be less desirable in some instances since it will increase the likelihood that the 911 system may be erroneously activated. Accordingly, it is contemplated that providing a delay in the activation of the 911 system would be preferable since it would tend to eliminate false activations of the emergency response system.

Once the user arrives and interacts with the monitor 10 through, for example, user input 30, the monitor 10 will begin to provide instructions to the user to treat the infant for SIDS.

The following examples provide more specific information about the operation of the monitor 10 once the user arrives and interactions with the monitor 10.

In an embodiment where the SIDS monitor receives infant parameter data which does not correspond to the infant's cardiac signal, the user may be prompted via instruction output 23 to attempt to rouse the infant first. If that is not effective, the user may be prompted to call 911. Alternatively, the user may be instructed to press a user input button 30 which will enable the device to automatically contact 911. Thereafter, the user may be prompted to deploy the defibrillation electrodes. Once the defibrillation electrodes are deployed, the monitor 10 will determine the existence of a shockable rhythm. If a shockable rhythm is present, the monitor 10 will begin the instruction sequence for delivering a defibrillation shock, prompting the parent to deliver the shock when the device is ready. After the shock is delivered, the monitor 10 will again assess the heart rhythm to determine if the rhythm has returned to a normal cardiac rhythm. If the rhythm has returned to normal, the monitor 10 may then instruct the user on delivery of CPR. An example of a protocol for delivery of infant CPR is provided in co-pending application serial number 08/994,495 to Snyder et al. entitled "External Defibrillator with CPR Prompts and ACLS Prompts and Method of Use" the specification of which is incorporated herein.

In an embodiment where the SIDS monitor receives infant parameter data which corresponds to the infant's cardiac signal, if the monitor 10 has detected an abnormal cardiac rhythm the user will be instructed to remove the monitoring electrodes and to attach the defibrillation electrodes. The monitor 10 may again analyze the cardiac rhythm using the defibrillation electrodes. If a shockable rhythm is detected, the monitor 10 will begin the instruction sequence for delivering a defibrillation shock, prompting the user to deliver the shock when the device is ready. After the shock is delivered, the monitor 10 will again assess the heart rhythm to determine if the rhythm has returned to a normal cardiac rhythm. If the rhythm has returned to normal, the monitor 10 may then instruct the user on the protocol for deliver of CPR if required. The monitor 10 may be set-up to activate the 911 system in the same manner as discussed in the previous example.

In another embodiment where the SIDS monitor receives infant parameter data which corresponds to the infant's cardiac signal and is capable of functioning as an automatic external defibrillator, once the monitor 10 has detected an abnormal cardiac rhythm, the monitor 10 will begin delivering a defibrillation shock. After the shock is delivered, the monitor 10 will again assess the heart rhythm to determine if the rhythm has returned to a normal cardiac rhythm. The monitor 10 may also be set up so that it automatically activates the 911 system when a shockable rhythm is detected.

It will be appreciated by those of skill in the art that in an embodiment where the SIDS monitor 10 receives infant parameter data which corresponds to the infant's cardiac signal along with non-cardiac infant parameter data, the monitor will behave as described above with respect to the monitors which receives cardiac data.

It should be appreciated that the scope of the invention is not limited to the embodiments described above. Various modifications and alterations might be made by those skilled in the art without departing from the spirit and scope of the present invention.

What is claimed:

1. A method of operating a SIDS monitor comprising:
   monitoring an infant parameter; and
   determining whether the monitored parameter is an acceptable value;
      if the monitored value is an acceptable value, then continuing to monitor the infant parameter, or
      if the monitored parameter is not within an acceptable value, then activating an alarm to alert a caretaker of the onset of SIDS symptoms
   requesting interaction from the caretaker to terminate the alarm phase and begin the rescue prompt phase,
      if caretaker interaction is not detected, then continue requesting interaction, or
      if caretaker interaction is detected, then begin rescue prompting, prompting the caretaker in administration of first aid to the infant.

2. The method of claim 1, further comprising the step of: automatically activating an emergency medical response system.

3. The method of claim 2 wherein the emergency medical response system is activated concurrently with activating the alarm.

4. The method of claim 2 wherein the emergency medical response system is automatically activated after a predetermined period of time if a caretaker does not interact with the SIDS monitor.

5. The method of claim 2 wherein the emergency medical response system is activated upon user interaction with the SIDS monitor.

6. The method of claim 1 further comprising the step of storing the most recent monitored infant parameter data in memory.

7. The method of claim 6 wherein the infant parameter data stored in memory is the most recent 60 minutes of data.

8. The method of claim 6 further comprising the step of removing the monitored infant parameter data from the memory.

9. A method of operating a SIDS monitor comprising:
   monitoring an infant cardiac signal; and
   determining whether the monitored infant cardiac signal is an acceptable value:
      if the monitored infant cardiac signal is an acceptable value, then continuing to monitor the infant cardiac signal, or
      if the monitored infant cardiac signal is not within an acceptable value, then activating an alarm to alert a caretaker of the onset of SIDS symptoms
   determining whether the infant cardiac signal represents a shockable rhythm,
      if the infant cardiac signal is a shockable rhythm, begin instructing the caretaker to deliver a defibrillation shock, or
      if the cardiac signal is not a shockable rhythm, continuing to monitor the infant cardiac rhythm.

10. The method of claim 9 further comprising the step of: automatically activating an emergency medical response system.

11. The method of claim 10 wherein the emergency medical response system is activated concurrently with activating the alarm.

12. The method of claim 10 wherein the emergency medical response system is automatically activated after a predetermined period of time if a caretaker does not interact with the SIDS monitor.

13. The method of claim 10 wherein the emergency medical response system is activated upon user interaction with the SIDS monitor.

14. The method of claim 9 further comprising the step of storing the most recent monitored infant cardiac signal as data in memory.

15. The method of claim 14 wherein the infant cardiac signal data stored in memory is the most recent 60 minutes of data.

16. The method of claim 14 further comprising the step of removing the monitored infant cardiac signal data from memory.

17. A method of operating a SIDS monitor comprising:
   monitoring an infant cardiac signal; and
   determining whether the monitored infant cardiac signal is an acceptable value;
      if the monitored infant cardiac signal is an acceptable value, then continuing to monitor the infant cardiac signal, or
      if the monitored infant cardiac signal is not within an acceptable value, then activating an alarm to alert a caretaker of the onset of SIDS symptoms
   determining whether the infant cardiac signal represents a shockable rhythm,
      if the infant cardiac signal is a shockable rhythm, deliver a defibrillation shock, or
      if the infant cardiac signal is not a shockable rhythm, continuing to monitor the infant parameter.

18. The method of claim 17 further comprising the step of automatically activating an emergency medical response system.

19. The method of claim 18 wherein the emergency medical response system is activated concurrently with activating the alarm.

20. The method of claim 18 wherein the emergency medical response system is automatically activated after a predetermined period of time if a caretaker does not interact with the SIDS monitor.

21. The method of claim 18 wherein the emergency medical response system is activated upon user interaction with the SIDS monitor.

22. The method of claim 17 further comprising the step of storing the most recent monitored infant cardiac signal as data in memory.

23. The method of claim 22 wherein the infant cardiac signal data stored in memory is the most recent 60 minutes of data.

24. The method of claim 22 further comprising the step of removing the monitored infant cardiac signal data from memory.

* * * * *